(12) United States Patent
Lai et al.

(10) Patent No.: US 6,604,825 B2
(45) Date of Patent: Aug. 12, 2003

(54) HYBRID TRACKING SYSTEM

(76) Inventors: Ming Lai, P.O. Box 10845, Pleasanton, CA (US) 94588; Meijuan Yuan, 5615 Cedar Crest Ter., Dublin, CA (US) 94568

( * ) Notice: Subject to any disclaimer, the term of this patent is extended or adjusted under 35 U.S.C. 154(b) by 174 days.

(21) Appl. No.: 09/817,407

(22) Filed: Mar. 26, 2001

(65) Prior Publication Data

US 2001/0035938 A1 Nov. 1, 2001

Related U.S. Application Data (60) Provisional application No. 60/194,170, filed on Apr. 3, 2000.

(51) Int. Cl.[7] .................................................. A61B 3/14
(52) U.S. Cl. ...................................................... 351/210
(58) Field of Search ................................ 351/205, 209, 351/210, 216, 217, 246, 206, 208, 221; 606/4, 5, 10; 250/235; 356/445–447; 359/385

(56) References Cited

U.S. PATENT DOCUMENTS

| | | |
|---|---|---|
| 4,764,005 A | 8/1988 | Webb et al. |
| 5,098,426 A | 3/1992 | Sklar et al. |
| 5,345,281 A | 9/1994 | Taboada et al. |
| 5,360,424 A | 11/1994 | Klopotek |
| 5,410,376 A | 4/1995 | Cornsweet et al. |
| 5,430,505 A | 7/1995 | Katz |
| 5,620,436 A | 4/1997 | Lang et al. |
| 5,632,742 A | 5/1997 | Frey et al. |
| 5,645,550 A | 7/1997 | Hohla |
| 5,752,950 A | 5/1998 | Frey et al. |
| 5,782,822 A | 7/1998 | Telfair et al. |
| 5,865,832 A | * 2/1999 | Knopp et al. ............... 351/209 |
| 5,943,117 A | 8/1999 | Van de Velde |
| 5,966,197 A | * 10/1999 | Yee ............................ 351/210 |
| 6,179,422 B1 | * 1/2001 | Lai ............................. 351/210 |
| 6,283,954 B1 | * 9/2001 | Yee ............................ 351/210 |
| 6,299,307 B1 | * 10/2001 | Oltean et al. ............... 351/210 |
| 6,367,931 B2 | * 4/2002 | Lai ............................. 351/209 |
| 2001/0022648 A1 | * 9/2001 | Lai ............................. 351/209 |
| 2002/0013573 A1 | * 1/2002 | Telfair et al. ................. 606/5 |

* cited by examiner

Primary Examiner—Marvin M. Lateef
Assistant Examiner—John R. Sanders (57) ABSTRACT

A hybrid tracking system is configured to combine the advantages of open loop and close loop tracking systems. The hybrid tracking system employs a position-sensing device in an open loop configuration, while the position-sensing device itself is a close loop device. A particular application of this tracking system is to track eye movement in a refractive laser surgery. The hybrid-tracking configuration enables optical and mechanical separation of the position-sensing device from the surgical laser beam. As a result, the position-sensing device can be made as a modular device, and the hybrid eye-tracking system can have a relatively large tracking range even when a curved mark such as the limbus is used as the tracking reference.

15 Claims, 8 Drawing Sheets

HYBRID TRACKING SYSTEM

This application claims the benefit of U.S. provisional application No. 60/194,170, filed on Apr. 3, 2000.

TECHNICAL FIELD

The present invention relates to an optical tracking system that tracks the lateral displacement of an object. In particularly, the present invention relates to a hybrid optical tracking system that tracks the lateral displacement of a subject's eye during a laser refractive surgery.

BACKGROUND

In a recent patent application entitled "Optical Tracking Device" and now U.S. Pat. No. 6,179,422, a tracking device is described to employ two scanning beams to scan across a reference mark affixed on an object to be tracked. In an embodiment of eye tracking, the device projects two beams scanning across the limbus at 12 and 3 o'clock positions, respectively.

Two configurations have been described in U.S. Pat. No. 6,179,422. The first one is of open loop, in which the scanning probe beam does not follow the movement of the eye. The second one is of close loop, in which both the surgical laser beam and the probe beam follow the movement of the tracked eye.

The advantage of the open loop configuration is its simplicity and its feasibility to separate the position-sensing device from the optical assembly for the surgical laser beam. Its disadvantage is a limited tracking range due to the curved nature of the limbus, which is the tracking mark for the position-sensing device. The movement detection along two orthogonal directions is no longer independent in an open loop configuration when the probe beams have significant displacement with respect to the curved mark such as the limbus.

In contrast, the close loop configuration can have much larger tracking range while having both the probe beam and the surgical beam deflected via a common beam steering module. The movement detection along the two orthogonal directions is basically independent in a close loop configuration because the probe beams have no significant displacement with respect to the limbus. On the other hand, using a common beam steering module for both the surgical and the probe beams introduces a couple of limitations. First, it requires a more complex optical assembly for the surgical laser beam. Second, it requires a bigger mirror for the common beam steering module, while a bigger mirror means a slower response.

SUMMARY

In this application, a hybrid configuration is contemplated to obtain an eye-tracking system having combined advantages of open loop and close loop configurations. The eye-tracking system with such hybrid configuration has an optical assembly of the position-sensing device separated from the optical assembly of the surgical laser beam. The position-sensing device can thus be made as a modular device and serve as an open loop device with respect to the whole tracking system. Meanwhile, the position-sensing device itself includes a beam steering module to direct the probe beams to follow the eye movement, and it can thus provide a larger tracking range. In term of its feedback mechanism, the position-sensing device itself is, therefore, a close loop device.

In a preferred embodiment, the hybrid tracking system consists of a position-sensing device, a system computer, and a first beam steering module. The position-sensing device detects the eye movement and produces x-y position signals of the eye. The system computer reads in the position signals and generates a control signal to the first beam steering module. The first beam steering module thus steers a surgical laser beam to follow the eye movement.

In the preferred embodiment, the position-sensing device comprises a first and a second scanning beam generators, a second beam steering module, an optical assembly, a first and a second photo detectors, a processing electronics, and a control unit. Each scanning beam generator produces a scanning probe beam. The second beam steering module directs the first and second scanning probe beams on to the eye such that the two beams scan repetitively across the limbus at 12 and 3 o'clock positions, respectively. The optical assembly focuses scattered light of the probe beams on to respectively the first and second photo detectors. As each probe beam scans across the limbus, the corresponding detector records a sharp change in the scattered light signal. The timing of this sharp change in the detector signal indicates the relative position between the scanning probe beam and the limbus. The processing electronics measures this timing with respect to a reference time position to produce a delay time Td. The control unit analyzes this delay time Td to generate a driven signal Vd to steer the second beam steering module such that the delay time Td is kept around an initial value $Td_0$. By this way, the scanning probe beam follows the movement of the eye, and the position-sensing device works as a close loop device.

When the response speed of the position-sensing device including the second beam steering module is fast enough to follow the eye movement, the driven signal Vd is proportional to the displacement of the eye. This signal Vd can then be used directly as x-y positioning signals of the eye. If the second beam steering module is slower than the involuntary eye movement, the eye displacement with respect to its initial position can be determined by measuring simultaneously the angular position $\alpha$ of the second beam steering mirror and the delay time Td. The control unit analyzes $\alpha$ and Td for the two probe beams and generates x-y positioning signals of the eye.

The surgical system computer can then use these x-y-positioning signals to guide the surgical laser beam to follow the eye movement. In this way, the position-sensing device feeds one-way signals to the surgical laser system and the system thus works in an open loop configuration.

Accordingly, an advantage of this hybrid-tracking system is its optical and mechanical separation of its position-sensing device from the other part of the tracking system and thus enables to design the position-sensing device into a modular device.

Another advantage of this hybrid-tracking system is its close loop configuration in detection, which enables a large tracking range for a moving object with a curved reference.

A further advantage of this hybrid-tracking system is its position detection scheme, which makes fast eye tracking (i.e., positioning detection) achievable even a relatively slow beam steering module is used in the position-sensing device.

The preferred embodiment is described in term of tracking a section of limbus as a reference. The disclosed method and apparatus can, however, be used to track other object with a curved reference. The above and other objectives and advantages of the invention will become more apparent in the following drawings, detailed description, and claims.

DETAILED DESCRIPTION

Figure 6:
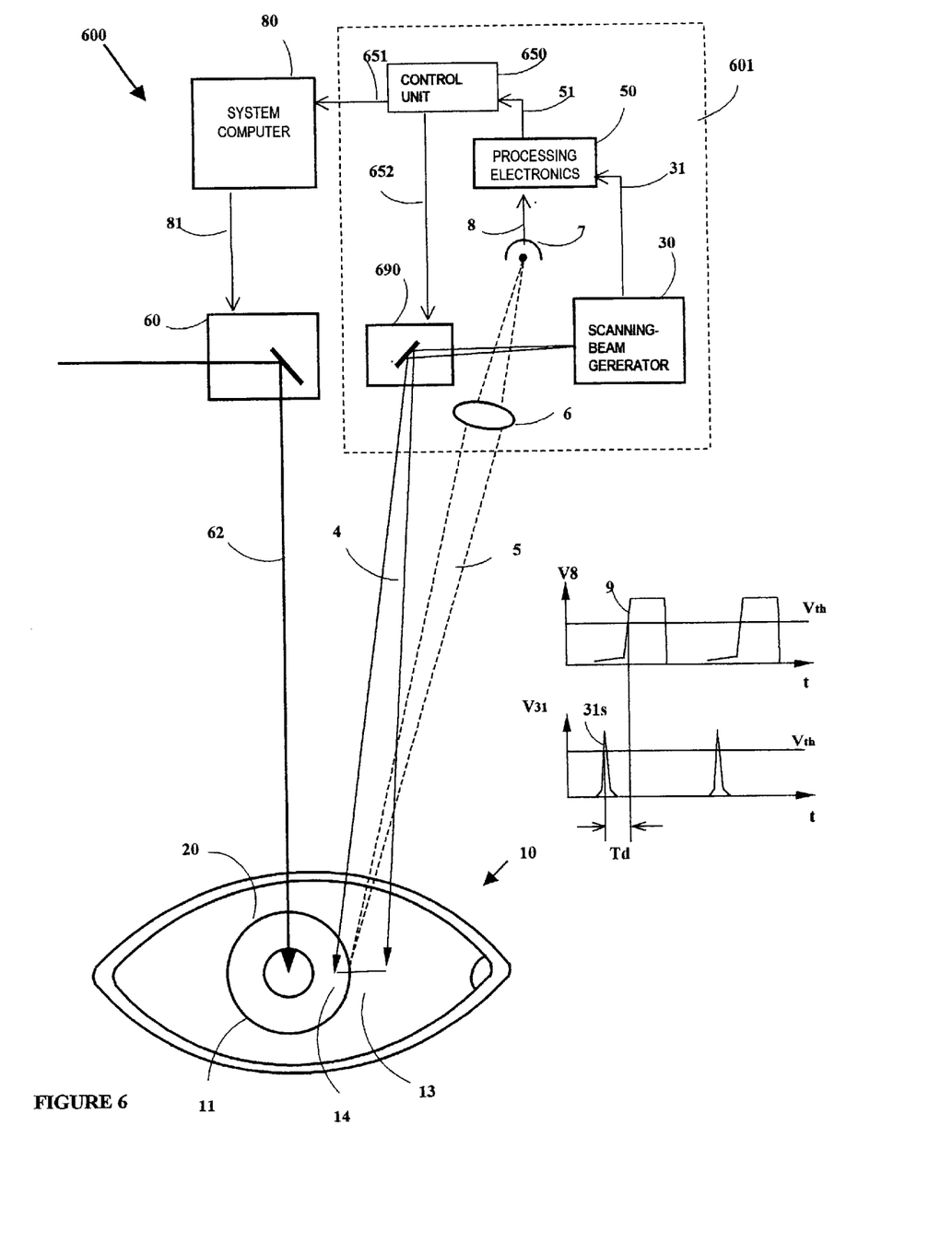
FIG. 6 is an embodiment of the hybrid tracking system in accordance with the present invention.

FIG. 6 is an embodiment of a hybrid tracking system 600 in accordance with the present invention. In comparison, FIG. 1 shows an open-loop configuration of a tracking system 100, and FIG. 2 shows a close-loop configuration of a tracking system 200.

Figures 1, 1A:
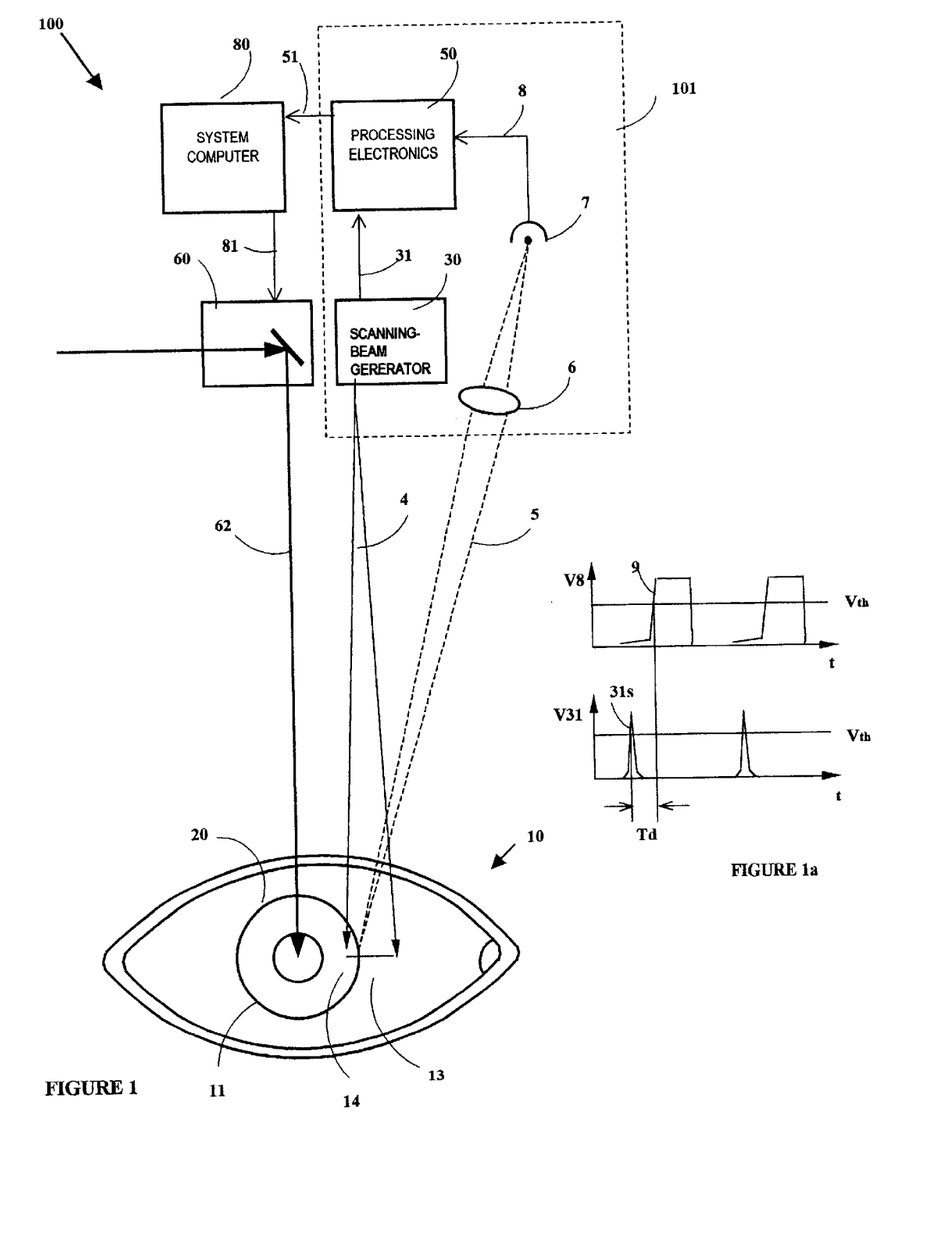
FIG. 1 shows an open-loop configuration of a tracking system.
FIG. 1a shows timing diagrams of the scattered-light signal from the eye and the reference signal generated by a scanning beam generator.
Figure 2:
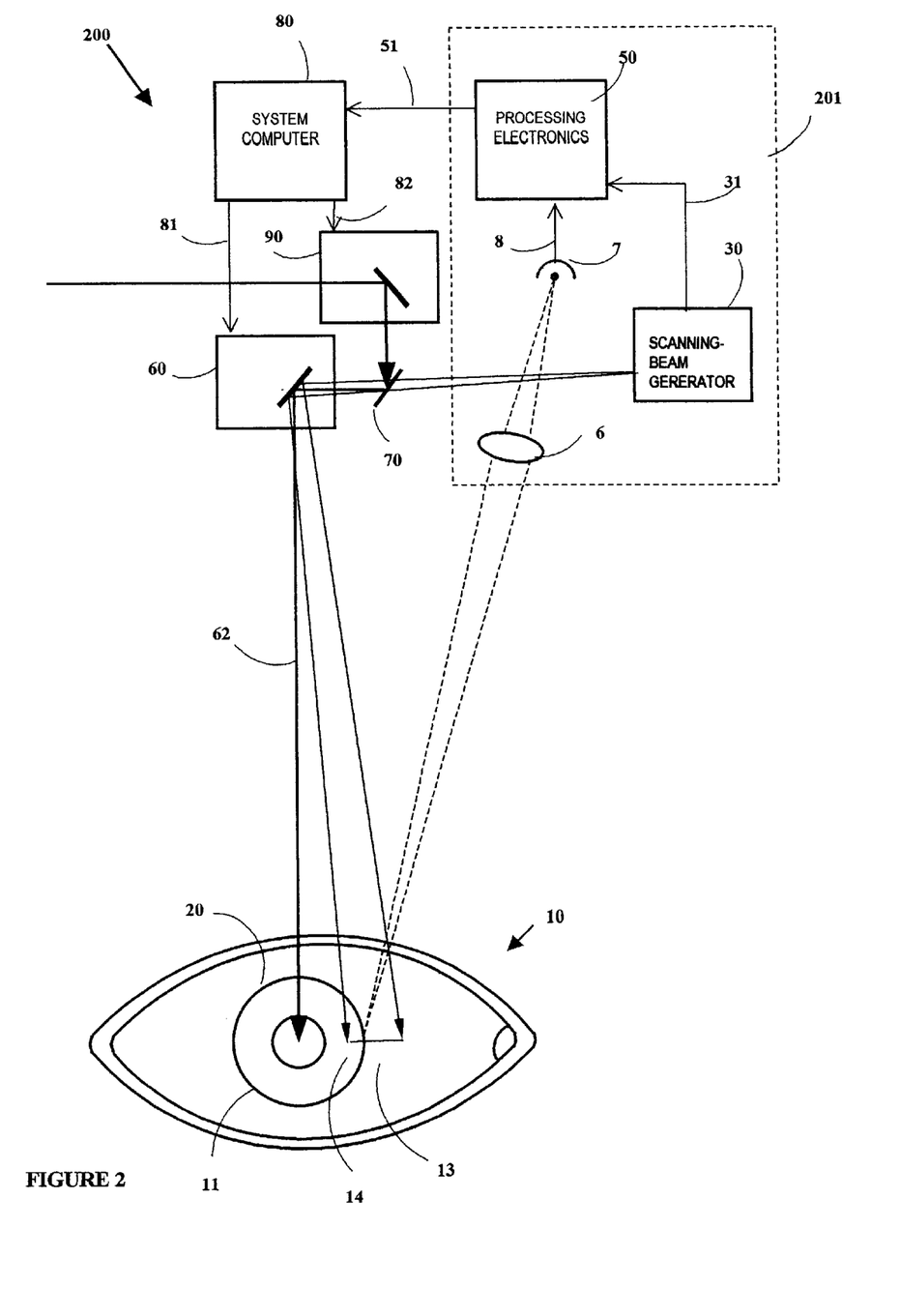
FIG. 2 shows a close-loop configuration of a tracking system.

Now refer to FIG. 1. The system 100 implements an open loop configuration that includes a position sensing device 101, a system computer 80, and a beam steering module 60 (e.g., a x-y scanner). The position-sensing module 101 projects a scanning probe beam 4 and monitors the position of the eye 10. The system computer 80 controls the beam steering module 60 to guide a surgical laser beam 62 to a desired position on the eye 10. As an open loop configuration, the scanning probe beam 4 dose not follow the movement of the eye 10 and only one beam steering module 60 is required.

For illustration purpose, the position-sensing device 101 shown in FIG. 1 is only a linear positioning device and is for monitoring one-dimensional eye movement only (e.g., along x-direction). To determine the eye's movement in two dimensions, a second set of linear positioning device is needed to monitor the movement of the eye 10 along a second different direction, e.g., the y-direction orthogonal to the x-direction.

The position-sensing device 101 comprises a scanning beam generator 30, a collection lens 6, a photo-detector 7, and a processing electronics 50. The limbus 11 of the eye 10 is used as a reference mark 20. The scanning-beam generator 30 projects a scanning probe beam 4 across the reference mark 20. The scanning probe beam 4 may repeatedly start from a fixed point and is scanned at a constant speed over a predetermined tracking range. The scanning-beam generator 30 also produces a reference signal 31 to indicate a reference point of the scanning.

The collection lens 6 is disposed at a proper position relative to the eye 10 to collect the scattered light 5 of the probe beam 4 and focuses the scattered light 5 onto photo-detector 7. The photo-detector 7 receives and converts the scattered light 5 into an electrical signal, i.e., scattered-light signal 8. The scattering from the sclera side 13 of the eye 10 is approximately 20 times stronger than that from the transparent cornea side 14. Hence, the intensity of the scattered light 5 exhibits a significant change when the probe beam 4 scans across the limbus 11. This intensity change of the scattered light 5, in turn, generates a sharp step in the scattered-light signal 8. The timing of this sharp step depends on the position of the eye 10.

In one implementation, an infrared laser beam (at 830 nm) of about 100 $\mu$W is used as the scanning probe beam 4 and the collection lens 6 having an aperture of about 18 mm is located about 30 cm away from the eye 10. Detector 7 receives a scattered-light power of about 20 nW when the probe beam 4 is on the sclera side.

FIG. 1a shows timing diagrams of the scattered-light signal 8 and the reference signal 31. The scattered-light signal 8 has a sequence of sharp steps and each sharp step 9 corresponds to a scan of the probe beam 4 across the limbus 11. The sharp step 9 has a time delay Td with respect to the reference point 31s of the scanning. This time delay Td depends on the position of the limbus 11 and varies as the eye 10 moves. The processing electronics 50, which may include a microprocessor, processes the reference signal 31 and the scattered-light signal 8 to determine this time delay Td for each scan. This time delay Td is then used to determine the position of the limbus 11. The lines Vth represent the threshold voltage for triggering.

To operate the tracking system 100, an initial time delay $Td_0$ or eye position is first registered and stored in the system computer 80. The time delay Td of subsequent scans is then compared with the initial time delay $Td_0$ to calculate a displacement of the eye 10. With this calculated displacement, the system computer 80 can generate a control signal 81 to drive the beam steering module 60 to steer the surgical laser beam 62 to follow the movement of the eye 10.

As an open loop device, the scanning probe beam 4 does not move with the eye 10. The beam steering module 60 can be used simultaneously to compensate the eye movement and to scan the surgical laser beam 62 on the eye 10. In this case, the control signal 81 may consist of a scanning signal and an offset signal. The scanning signal scans the surgical laser beam 62 in a predetermined pattern while the offset signal offsets the scanning to compensate for the eye movement. This open-loop tracking system 100 is relatively simple and is good for tracking small movement of the eye 10.

FIG. 2 shows a schematic diagram of a close-loop tracking system 200. In the close-loop configuration, both the scanning beam 4 and the surgical beam 62 are steered to the eye 10 by a common steering module 60. Consequently, both the scanning probe beam 4 and the surgical laser beam 62 follow the movement of the eye 10.

In implementation, the scanning probe beam 4 is directed into the first beam steering module 60 and reflected onto the reference mark 20 (i.e. the limbus 11). A dichromatic mirror 70 is placed in the path of the scanning probe beam 4 to couple the surgical laser beam 62 into the first beam steering module 60. The dichromatic mirror 70 reflects light at the wavelength of the surgical laser beam 62 but transmits light at the wavelength of the scanning probe beam 4. The surgical laser beam 62 is reflected from the first beam steering module 60 and projected onto the eye 10.

Again, the scattered light 5 from the reference mark 20 is collected by a lens 6 and detected by a photo-detector 7, which produces an output of scattered-light signal 8. Similar to the open loop system 100, the scatted-light signal 8 has a sharp step 9 corresponding to each scan of the probe beam 4 across the boundary of the reference mark 20. The sharp step 9 has a time delay Td with respect to the reference point 31s of corresponding scan. A processing electronics 50 determines this time delay Td for each scan.

To operate the tracking system 200, an initial time delay $Td_0$ or eye position is first registered and stored by the system computer 80. The time delay Td of later scans is then compared with the initial time delay $Td_0$. Any deviation of Td from $Td_0$ is used as an error signal to drive the first beam steering module 60 such that to bring the error signal toward zero. Through this process, the first beam steering module 60 deflects the scanning probe beam 4 to follow the movement of the eye 10. Seeing the same deflection as the scanning probe beam 4, the surgical laser beam 62 can thus impinge on any predetermined position of the eye 10 as if the eye remains stationary.

As a close loop device, the relative position between the trace of the scanning probe beam 4 and the reference mark 20 is kept constant during the operation. The first beam steering module 60 is thus used solely for compensating the eye movement. A second beam steering module 90 is required to scan the surgical laser beam 62 on the eye 10 for surgery purpose. In this case, the control signal 81 to first beam steering module 60 is simply the driving signal to compensate the eye movement. The control signal 82 to second beam steering module 90 is simply the programmable signal to scan the surgical laser beam 62. The close loop device 200 is relatively more complicate but it can track a relative large displacement of the eye 10.

Figure 3A:
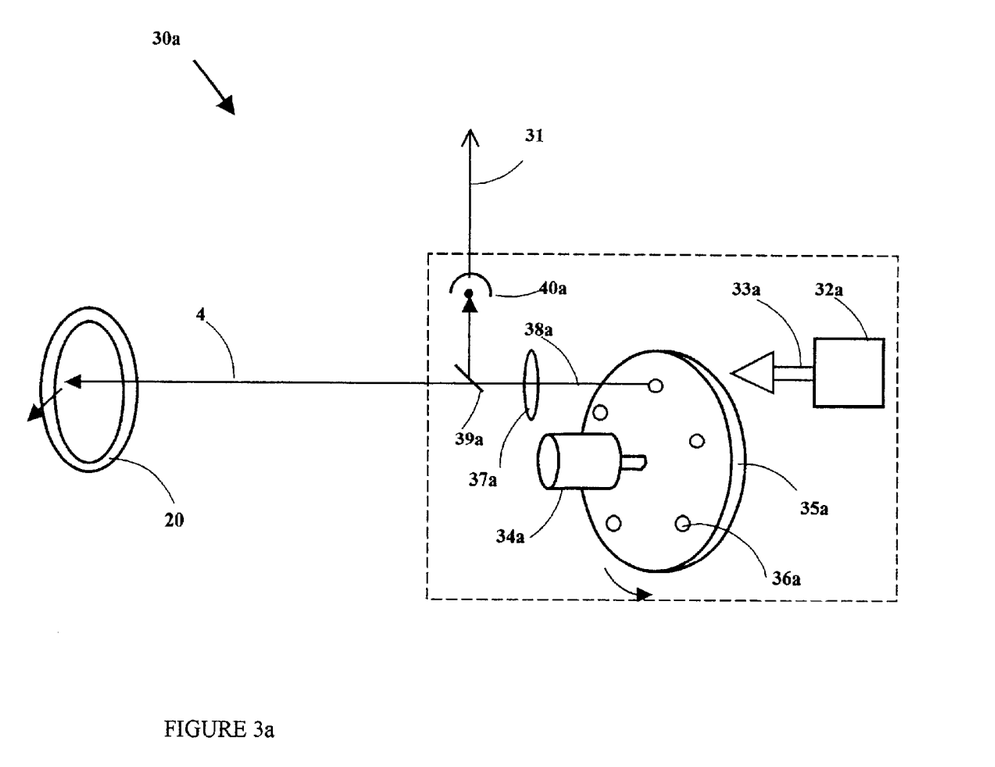
FIG. 3a is a schematic diagram showing a scanning-beam generator.

FIG. 3a shows a scanning-beam generator 30a that produces a scanning probe beam 4a. The generator 30a includes an infrared-light source 32a, which produces an infrared-light beam 33a projected onto a rotating blade 35a. The blade 35a has a set of pinholes 36a evenly distributed on a circle. A motor 34a drives the blade 35a at a constant rotation speed. The pinholes 36a are thus scanned across the infrared-light beam 33a at a constant speed.

A lens 37a focuses onto a reference ring 20 (i.e. the reference mark) the infrared-light beam 38a that is transmitted through the pinhole 36a. As the pinhole 36a is scanned across the infrared beam 33a, the image of the pinhole 36a is scanned across the reference ring 20. Thus, the transmitted infrared beam 38a may serve as the scanning probe beam 4 of FIG. 1.

A beam splitter 39a directs a small portion of the beam 38a onto a reference photo-detector 40a. This reference photo-detector 40a has a tiny light-sensitive area and the detected signal is thus a sequence of spikes as the split beam scans across the reference detector repetitively. The output signal from the photo-detector 40a defines a reference point of the scanning and serves as the reference signal 31 of FIG. 1.

In this embodiment, the infrared-light source 32a can be simply a light emitted diode. The repetition rate of the scanning probe beam 4 can be up to the kilohertz range. For example, the motor 34a may run at 100 rotation per second and the blade 35a may have 10 pinholes 36a on it.

Figure 3B:
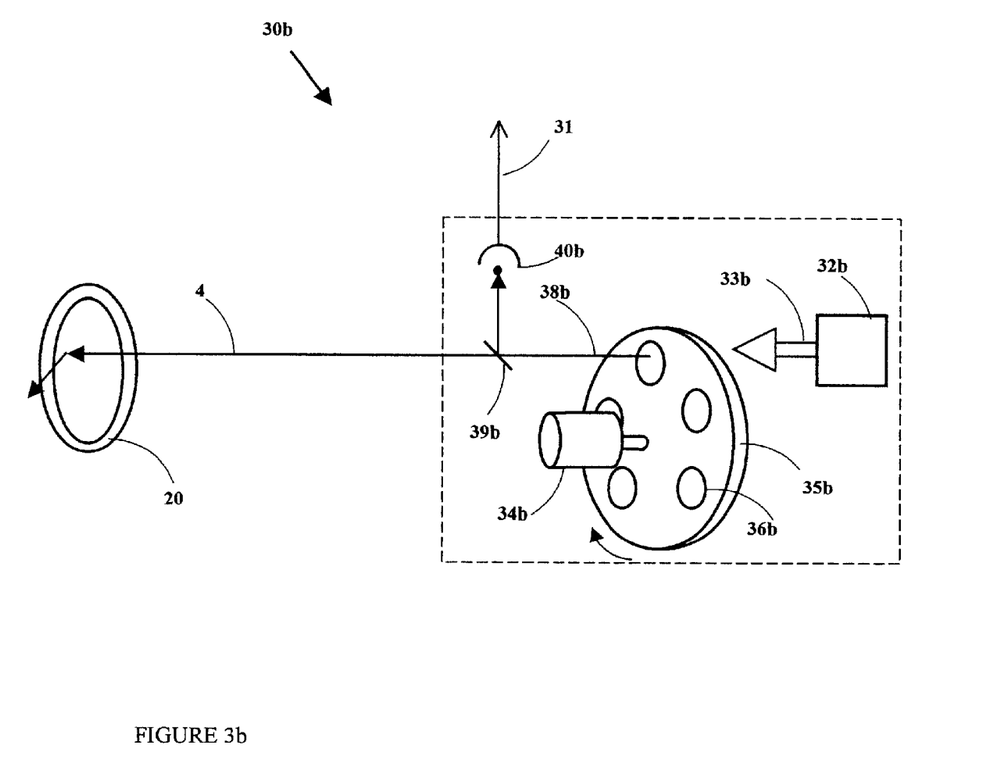
FIG. 3b is a schematic diagram showing another scanning-beam generator.

FIG. 3b shows another scanning-beam generator 30b producing a scanning probe beam 4. The generator 30b includes an infrared-light source 32b, which produces an infrared-light beam 33b directed onto a disk 35b. The disk 35b holds a set of identical lenses 36b evenly distributed on a circle. A motor 34b rotates the disk 35b and the lenses 36b are scanned across the infrared-light beam 33b at a constant speed.

The infrared-light beam 38b transmitted through a lens 36b is focused onto a reference ring 20. As the lens 36b is scanned across the infrared-light beam 33b, the focused beam 38b is scanned across the reference ring 20. Thus, the focused infrared-light beam 38b may serve as the scanning probe beam 4 of FIG. 1.

Again, a beam splitter 39b directs a small portion of the beam 38b onto a reference photo-detector 40b. The output signal from the photo-detector 40b defines a reference point of the scanning and serves as the reference signal 31 of FIG. 1. In this embodiment, the infrared-light source 32b is preferably either a pre-focused beam or a point source.

Figure 4:
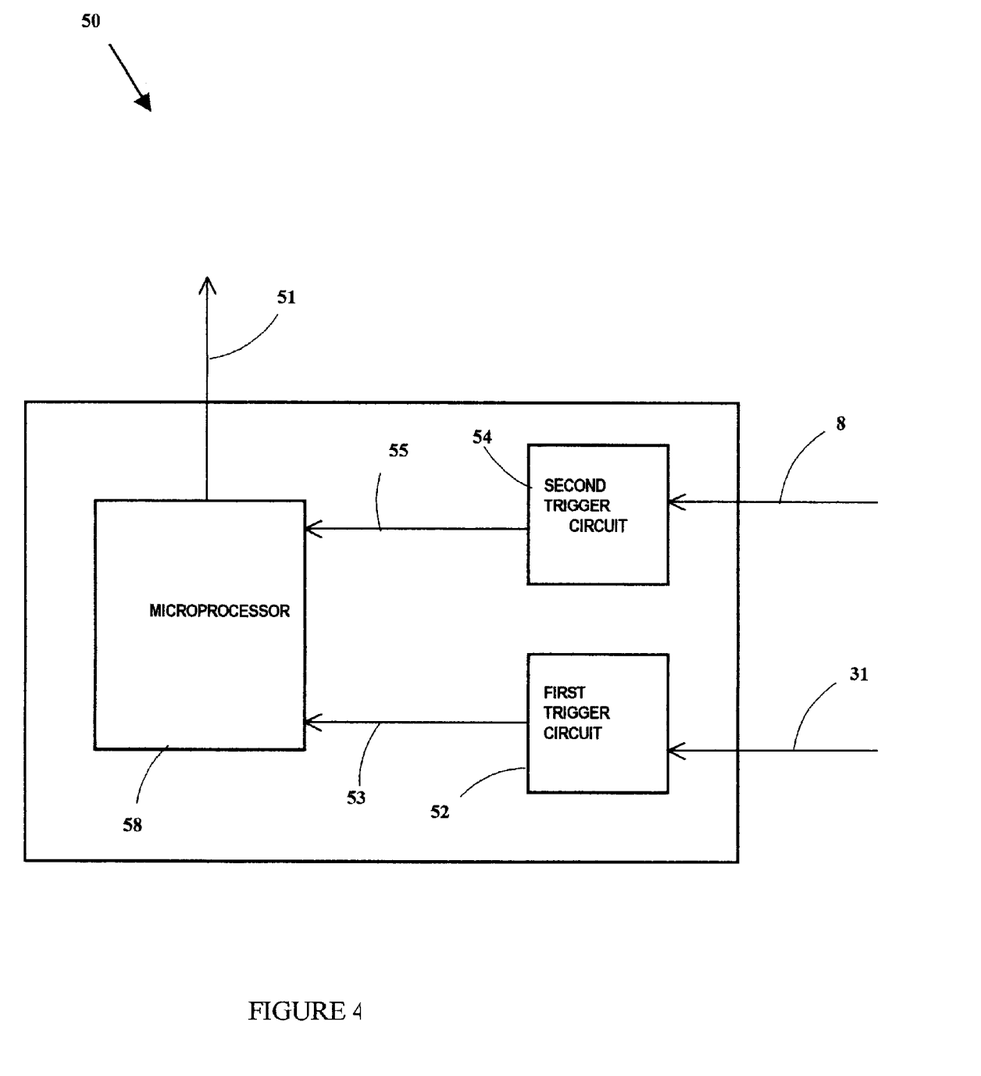
FIG. 4 is a block diagram showing a processing electronics for the optical monitoring and tracking systems of FIGS. 1 and 2.

FIG. 4 is a block diagram showing one embodiment of the processing electronics 50. This processing electronics 50 includes a first trigger circuit 52, a second trigger circuit 54, and a microprocessor 58. The reference signal 31 from the scanning beam generator 30 is fed into the first trigger circuit 52 to produce a TTL output signal 53 carrying the timing of the reference signal 31. The scattered-light signal 8 from the photo-detector 7 is fed into the second trigger circuit 54 to produce a TTL output signal 55 carrying the timing of the scattered-light signal 8.

The microprocessor 58 reads in the signal 53 and signal 55 to calculate a time delay Td between the two signals. This time delay Td indicates the relative position of the reference mark 20 to the scanning probe beam 4. This delay Td can be compared with an initial delay $Td_0$ registered and stored by the system computer 80 at the very beginning of the tracking.

For an open loop system 100, any change of the delay Td from its initial value $Td_0$ can be used to determine a displacement of the eye 10 from its initial position. The determined displacement can then be converted into an offset signal combined in the control signal 81 to deflect the surgical laser beam 62 to follow the movement of the eye 10.

For a close loop system 200, any deviation of the delay Td from its initial value $Td_0$ is used as an error signal to drive the first beam steering module 60 such that to bring the error signal toward zero. The first beam steering module 60 thus deflects both of the scanning probe beam 4 and the surgical laser beam 62 to follow the movement of the eye 10.

The above-described operation of the processing electronics 50 is repetitively for every scan of the probe beam 4. The first trigger circuit 52 and the second trigger circuit 54 should be reset automatically after the signal 53 and signal 55 are read by the microprocessor 58.

The processing electronics 50 shown in FIG. 4 is for one axis tracking. To track the two-dimensional movement of the eye 10, another pair of the trigger circuit should be used.

Figure 5A:
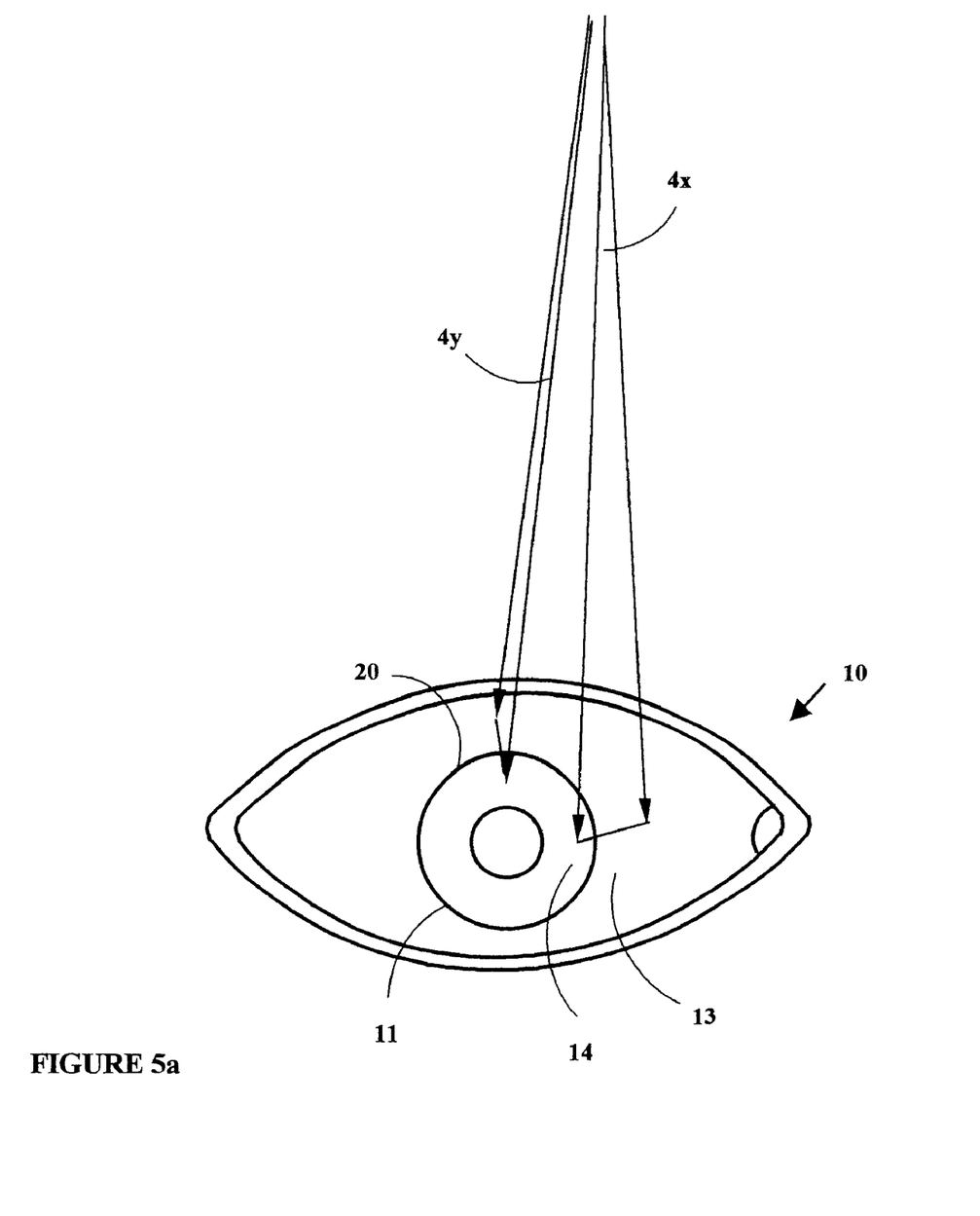
FIG. 5a is a schematic diagram illustrating simultaneous tracking of an eye in two different directions by two scanning probe beams projected on the limbus.

FIG. 5a shows schematically two scanning probe beams 4x and 4y projected on a reference ring 20 (the limbus 11) for two-dimension positioning detection. The two scanning probe beams 4x and 4y are set along two approximately perpendicular directions and occupy about one quart of the limbus 11.

Figure 5B:
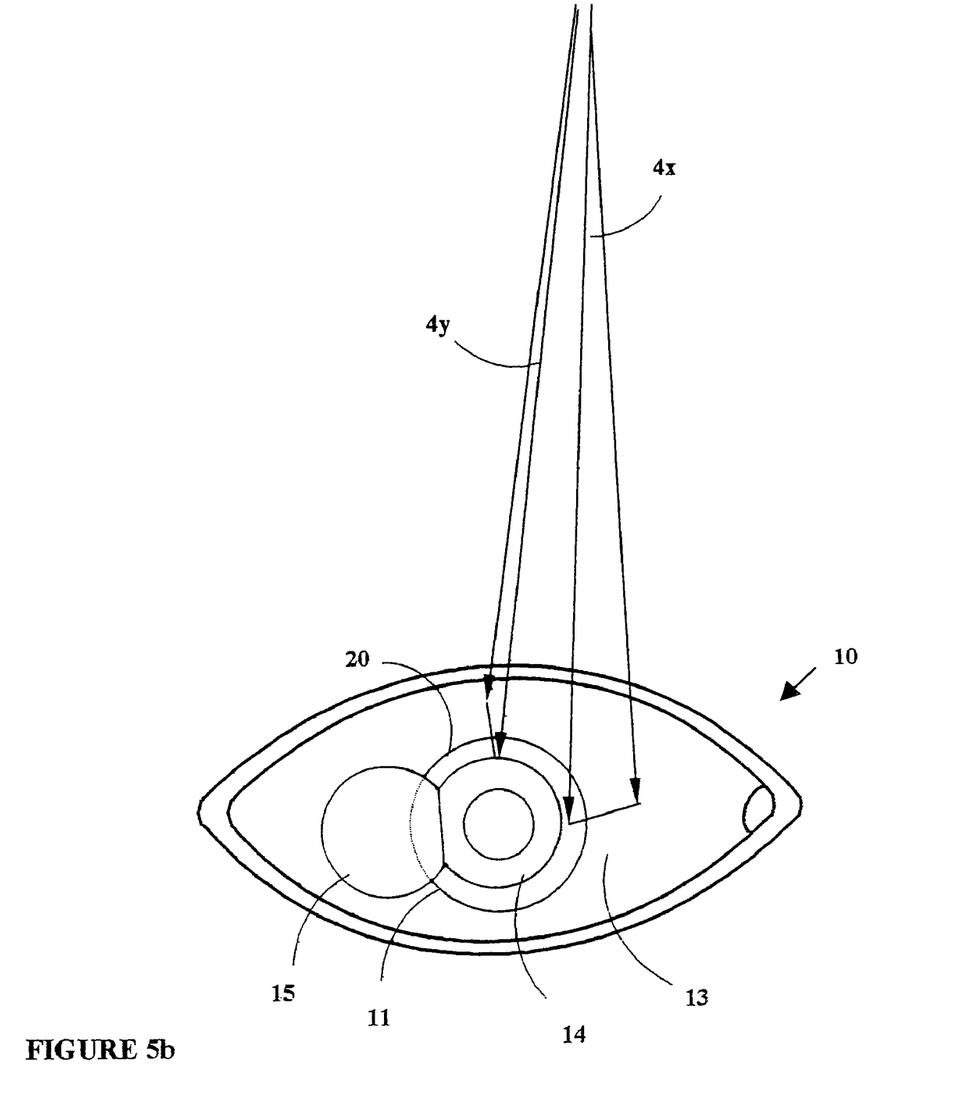
FIG. 5b shows two scanning probe beams projected on a partially obscured limbus to track the eye movement in two different directions in a LASIK surgery.

FIG. 5b shows how the present tracking systems remain fill performance for LASIK. In a LASIK surgery, a disk shape flap is laminated from the cornea and about one quart of the perimeter is uncut to maintain the flap attached to the cornea. The flap is folded over during the surgery to allow laser ablation on the corneal bed. The folded flap 15 covers about one third of the limbus 11 and may disable those eye tracking devices which rely on the whole limbus as the reference. The corneal bed after the flap is folded becomes less smooth and the scattered light from the corneal bed may disturb those tracking devices that use the pupil as a reference.

As illustrated in FIG. 5b, the two scanning beams 4x and 4y use only the limbus section that is not covered by the cornea flap 15. Therefore, the limbus 11 remains as a good reference for the present tracking systems.

FIG. 6 is an embodiment of the hybrid tracking system 600 in accordance with the present invention. The system 600 has a hybrid configuration of FIG. 1 and FIG. 2 and combines the advantages of open loop and close-loop configurations.

The hybrid tracking system 600 implements an open loop configuration that includes a position sensing device 601, a system computer 80, and a first beam steering module 60. The position sensing device 601 itself is, however, a close-loop device. The device 601 projects two scanning probe beams 4x and 4y as shown in FIG. 4 and monitors the position of the eye 10. As a close loop device, the scanning probe beams 4x and 4y follow the movement of eye 10.

For illustration purpose, the position-sensing device 601 shown in FIG. 6 is only a linear positioning device and is for monitoring one-dimensional eye movement only (e.g., along x-direction). To determine the eye's movement in two dimensions, a second set of linear positioning device is needed to monitor the movement of the eye 10 along a second different direction, e.g., the y-direction orthogonal to the x-direction.

The position-sensing device 601 comprises a scanning beam generator 30, a second beam steering module 690, a collection lens 6, a photo-detector 7, a processing electronics 50, and a control unit 650. The scanning-beam generator 30 generates a scanning probe beam 4. The probe beam 4 is directed to the second beam steering module 690 and then projected across the reference mark 20. The scanning probe-beam 4 scans repeatedly at a substantially constant speed. The scanning-beam generator 30 also produces a reference signal 31 to indicate a reference point of the scanning.

Once again, the scattered light 5 from the reference mark 20 is collected by the collect lens 6 and detected by the photo-detector 7, which produces an output of scattered-light signal 8. Similar to the open loop system 100, the scatted-light signal 8 has a sharp step 9 corresponding to each scan of the probe beam 4 across the boundary of the reference mark 20. The sharp step 9 has a time delay Td with respect to the reference point 31s of corresponding scan. The processing electronics 50 determines this time delay Td for each scan.

To operate the position-sensing device 601, an initial time delay $Td_0$ or eye position is first registered and stored by the control unit 650. The time delay Td of later scans is then compared with the initial time delay $Td_0$. Any deviation of Td from $Td_0$ is used as an error signal. This error signal is integrated by the control unit 650 to produce a driven signal 652 to drive the beam steering module 690 such that to bring the error signal toward zero. Through this process, the second beam steering module 690 deflects the scanning probe beam 4 to follow the movement of the eye 10.

As a close loop device, position-sensing device 601 thus keeps substantially a constant position of the scanning probe beam 4 with respect to the reference mark 20 during the operation. By this way, the detection along the two orthogonal directions is basically independent and large tracking range can be obtained.

As an open loop configuration, the tracking system 600 has a position-sensing device 601 independent from the optical assembly of the surgical laser beam 62. The position-sensing device 601 can thus be assembled as a separated unit or a module.

The driven signal 652 is to drive beam steering module 690 to steer probe beam 4 to follow the eye movement. The beam steering module 690 can be a pair of galvanometers or a translatable lens. The driven signal 652 itself is thus a measure of the displacement of the tracked eye 10 from its initial position.

When the response speed of the position-sensing device 601 including the second beam steering module 690 is fast enough to follow the eye movement, the driven signal 652 is proportional to the displacement of the eye. This signal 652 can then be used directly as x-y positioning signals 651 of the eye. If the beam steering module 690 is slower than the involuntary eye movement, the eye displacement with respect to its initial position can be determined by measuring simultaneously the angular position α of the mirror of the second beam steering module 690 and the delay time Td. The control unit analyzes α and Td for the two probe beams and generates x-y positioning signals 651 of the eye.

The surgical system computer can then use these x-y-positioning signals 651 as an offset signal to the first beam steering module 60 to direct the surgical laser beam 62 to follow the eye movement. In this way, the position-sensing device 601 feeds one-way signals 651 to the surgical laser system and the system thus works in an open loop configuration.

The surgical laser beam 62 has a wavelength around 200 nm or 3 micron for refractive surgery. Obviously, this hybrid tracking system can be used for other eye surgery and diagnosis applications. For other eye surgery application, the surgical laser beam 62 is replaced with a laser beam of other wavelength and intensity.

For diagnosis application, the surgical laser beam 62 in FIG. 6 is replaced with a probe beam or an observation beam path to the eye 10. With this hybrid tracking system, the probe beam or observation beam path follows the eye movement and eye diagnosis can be done as if the eye is steady still.

Although the above embodiment is described with a specific reference to eye tracking, the techniques can be generally used to track lateral movement of other object with curved reference mark. Various modifications can be made without departing from the scopes of the appended claims.

What is claimed is:

1. A hybrid tracking system for tracking lateral movement of an object, comprising of:
   a closed-loop position sensing device projecting on said object a first scanning probe beam and a second scanning probe beam, wherein said first scanning probe beam scans linearly and repeatedly across a first position of a curved mark on said object and senses a first relative location of said curved mark along a first scanning direction of said first probe beam, and said second scanning probe beam scans linearly and repeatedly across a second position of said curved mark on said object and senses a second relative location of said curved mark along a second scanning direction of said second probe beam, wherein said first scanning direction and said second scanning direction are approximately perpendicular to each other, and wherein said closed-loop position sensing device employs a first beam steering module to actively maintain said first relative location and said second relative location as constants;
   a second beam steering module to direct a light beam onto said object; and
   a control unit coupled to said closed-loop position sensing device and generating a control signal to drive said second beam steering module as is in an open loop configuration, wherein said control signal consists of an offset signal to compensate for position change of said object;

wherein said second beam steering module directs said light beam to desired positions on said object regardless of any movement of said object.

2. The hybrid tracking system as in claim 1 wherein said object is a human eye and said curved reference mark is the limbus.

3. The hybrid tracking system as in claim 1 wherein said first and second scanning probe beams are in the near infrared spectrum.

4. The hybrid tracking system as in claim 1 wherein said first and second beam steering modules each consist of a galvanometer.

5. The hybrid tracking system as in claim 1 wherein said light beam is a surgical laser beam.

6. The hybrid tracking system as in claim 1 wherein said light beam is a diagnostic light beam.

7. A method for tracking lateral movement of an object, comprising the steps of:

projecting a first scanning probe beam scanning linearly and repeatedly across a first position of a curved mark on said object;

providing a first photo-detector circuit sensing a first relative location of said curved mark along a first scanning direction of said first scanning probe beam;

projecting a second scanning probe beam scanning approximately perpendicular to said first scanning probe beam and scanning linearly and repeatedly across a second position of said curved mark on said object;

providing a second photo-detector circuit sensing a second relative location of said curved mark along a second scanning direction of said second scanning probe beam;

providing a first beam steering module to direct said first scanning probe beam and said second scanning probe beam onto said object;

providing a first control unit coupled to said first and second photo-detectors and generating a first control signal to drive said first beam steering module to actively maintain said first relative location and said second relative location as constants;

providing a second beam steering module to direct a light beam onto said object; and providing a second control unit coupled to said first control unit and generating a second control signal to drive said second beam steering module, said second control signal consists of an offset signal to compensate for position change of said object;

wherein said second beam steering module directs said light beam to a desired position on said object regardless of any movement of said object.

8. A closed-loop position sensing device for sensing lateral movement of an object, comprising of:

a beam steering module;

a scanning beam generator to generate a first and a second scanning probe beams that are directed into said beam steering module and projected at two positions of a curved reference mark on said object, wherein said first and second scanning probe beams scan linearly and repeatedly across said curved reference mark at said two positions respectively, and wherein scattered light of each said probe beam has a sharp change when said probe beam scans across boundary of said reference mark;

an optical assembly collecting said scattered light of said first and second scanning probe beams from said object;

a first photo-detector receiving said scattered light of said first scanning probe beam to produce a first scattered-light signal indicating a first relative position of said reference mark along a first scanning direction of said first scanning probe beam;

a second photo-detector receiving said scattered light of said second probe beam to produce a second scattered-light signal indicating a second relative position of said reference mark along a second direction of said second scanning probe beam; and a control unit coupled to said scanning beam generator, said first and said second photo-detectors, and said beam steering module, to process said first and second scattered-light signals to determine said first and second relative positions and to control said beam steering module to maintain actively said first and second relative positions as constants;

wherein said first and second scanning probe beams follow any movement of said reference mark and said control unit generates positioning signals to indicate said movement of said reference mark.

9. The closed-loop position-sensing device as in claim 8 wherein said object is a human eye and said reference mark is the limbus.

10. The closed-loop position-sensing device as in claim 8 wherein said first and second scanning probe beams are in the near infrared spectrum.

11. The close-loop position-sensing device as in claim 8 wherein said beam steering module is a pair of galvanometers.

12. The closed-loop position-sensing device as in claim 8 wherein said beam steering module is a translatable lens.

13. The closed-loop position-sensing device as in claim 8 wherein said scanning beam generator includes a set of rotating pinholes.

14. The closed-loop position-sensing device as in claim 8 wherein said scanning beam generator includes a set of rotating lenses.

15. The closed-loop position-sensing device as in claim 8 wherein said first and second scanning beams scan across the limbus at 12 and 3 o'clock positions.

* * * * *